United States Patent [19]

Nauta

[11] 4,269,834

[45] May 26, 1981

[54] COPPER COMPLEXES OF ISOQUINAZOLINES

[76] Inventor: Wijbe T. Nauta, Rembrandtlaan 17, Nieuw Loosdrecht, Netherlands

[21] Appl. No.: 916,541

[22] Filed: Jun. 19, 1978

[30] Foreign Application Priority Data

Jun. 17, 1977 [GB]  United Kingdom ............... 25539/77
Dec. 15, 1977 [NL]  Netherlands ......................... 7713938

[51] Int. Cl.³ ...................... C07F 1/08; C07D 401/04; C07D 403/04; A61K 31/555
[52] U.S. Cl. .................................. 424/245; 426/532; 544/225; 544/284; 546/10; 546/143; 546/144; 546/336; 546/338; 546/329
[58] Field of Search .......................... 424/245; 546/10; 426/532

[56] References Cited

U.S. PATENT DOCUMENTS 3,980,654  9/1976  Gysling ................................. 546/10

FOREIGN PATENT DOCUMENTS 956241  4/1964  United Kingdom ...................... 546/10

OTHER PUBLICATIONS

Antic et al., Eur. J. Med. Chem. 1977, 573-575.
Antic et al., Chem. Abs. 88, 131386v (1977).
Shulman et al. I, Chem. Abs. 79, 74160e.
Shulman et al. II, Chem. Abs. 83, 142525n.

*Primary Examiner*—Mark L. Berch
*Attorney, Agent, or Firm*—Robert E. Burns; Emmanuel J. Lobato; Bruce L. Adams

[57] ABSTRACT

A method of combatting mycoplasma infections by treatment with copper complexes of certain phenanthroline, isoquinoline and quinazoline derivatives. A number of the complexes and ligand compounds are novel, therapeutically useful substances. Processes for their preparation are described.

16 Claims, No Drawings

COPPER COMPLEXES OF ISOQUINAZOLINES

SUMMARY OF THE INVENTION

This invention relates to therapeutically useful copper complexes of certain organic compounds, to compositions containing them, to their use in the treatment of mycoplasma infections in animals and plants and to processes for their preparation. The said organic compounds ("ligands") belong to the classes of phenanthroline, isoquinoline and quinazoline derivatives. Some of them are new and form a feature of the invention.

BACKGROUND OF THE INVENTION

Mycoplasmas are a group of microorganisms characterized by their small size and lack of a cell wall. A mycoplasma cell is bounded by a membrane, the chemical composition of which is similar to that of mammalian cells. Because of the difference between mycoplasmas and bacteria, antibacterial agents are not necessarily also effective against mycoplasmas. As the role of mycoplasmas in the aetiology of human, animal and plant diseases is more and more recognized, the fact that the number of chemotherapeutics active against these organisms is very limited makes the search for effective compounds worthwhile.

PRIOR ART

Many copper complexes of 1,10-phenanthrolines are already known in the literature. For instance in Canadian Pat. No. 824,652, German patent application ("Offenlengungsschrift") No. 2453624 and H. M. N. H. Irving et al., Anal. Chim.Acta, 55 (2), 315 (1971) (Chem.Abstr. 75,91834n) copper complexes of variously substituted 1,10-phenanthrolines are described that are active against micro-organisms such as bacteria, fungi and yeasts. Antimycoplasma activity is not disclosed in said publications. 1-Aminoisoquinolines and 4-aminoquinazolines having a heterocyclic substituent at the 3-, respectively 2-, position are described in U.S. Pat. Nos. 3,991,063 and 3,980,650. The compounds are stated to have antimycoplasma activity. Compounds in which the heterocyclic substituent is the 2-pyridyl group are particularly disclosed.

The Dutch patent application No. 7604849 relates to compounds of the general formula

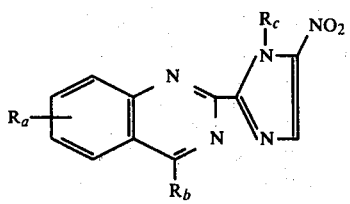

In which $R_a$ represents a hydrogen or halogen atom or a lower alkyl group, $R_b$ represents a lower alkyl, lower alkenyl or lower hydroxyalkyl group and $R_c$ represents a more complex substituent, for instance a group of one of the types aminoalkoxy, aminoalkylthio, morpholino, thiamorpholino, piperazino, morpholinoamino, thiamorpho-lino-amino, piperazino-amino. The compounds are stated to be active against parasites, such as amoebes, trichomonads and mycoplasmas.

DETAILED DESCRIPTION OF THE INVENTION

This invention relates to a method of combatting mycoplasma induced diseases in animals, including humans, and plants which comprises treating the animal or plant with a complex of a copper salt, having an acceptable anion, with an organic compound of the general formula

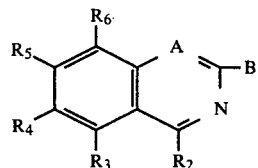

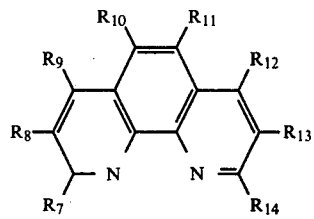

wherein A represents a nitrogen atom or a —CR— group, in which R represents a hydrogen atom or an alkyl group with at most 12 caron atoms, B represents a group of the formula

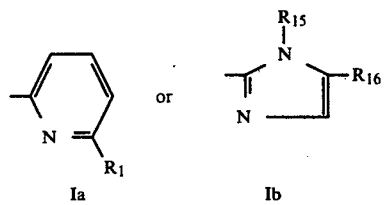

in which $R_1$ represents a hydrogen atom or a lower alkyl group, $R_{15}$ represents a hydrogen atom or a lower alkyl or lower alkenyl group and $R_{16}$ represents a hydrogen atom or a nitro group, $R_2$ represents a hydrogen or halogen atom or a lower alkyl, phenyl, amino, lower alkylamino or di(lower alkyl)-amino group, with the proviso that $R_2$ is hydrogen, halogen, methyl, amino, lower alkylamino or di(lower alkylamino) when A is a nitrogen atom and/or when B is a group of formula Ib, $R_3$ and $R_6$ are the same or different and each represents a hydrogen or halogen atom or a lower alkyl group, $R_4$ and $R_5$ are the same or different and each represents a hydrogen or halogen atom, an alkyl group having at most twelve carbon atoms or a lower alkoxy group, $R_7$ and $R_{14}$ are the same or different and each represents a hydrogen or halogen (preferably chlorine) atom or a lower alkyl, lower alkoxy or amino group and $R_8$, $R_9$, $R_{10}$, $R_{11}$, $R_{12}$ and $R_{13}$ are the same or different and each represents a hydrogen atom or a lower alkyl group. The terms "lower alkyl", "lower alkenyl" and "lower alkoxy" in this specification refer to groups with at most 6 carbon atoms.

By the term "acceptable anion" as used in this specification is meant an anion which is relatively innocuous to the animal or plant to be treated at the dosage used so that the anti-mycoplasma effect of the copper complex is not vitiated by side-effects ascribable to the anion.

Preferred compounds of formula I are those in which A represents a —CH— group, $R_2$ represents a lower alkyl (preferably methyl or ethyl) or amino group, $R_6$ represents a halogen or hydrogen atom and $R_3$, $R_4$ and $R_5$ represent hydrogen atoms. Preferred halogen atoms, and alkyl or alkoxy groups within the definitions of $R_3$, $R_4$, $R_5$ and $R_6$ are chlorine, and methyl and methoxy.

Preferred compounds of formula II are those in which $R_7$ and $R_{14}$ are the same or different and each represents a lower alkyl (preferably methyl) or amino group and $R_8$, $R_9$, $R_{10}$, $R_{11}$, $R_{12}$ and $R_{13}$ represent hydrogen atoms. When the symbols $R_8$ to $R_{13}$ do not all represent hydrogen, preferably at most four of them represent methyl or ethyl and the others represent hydrogen.

Complexes of the compounds of formulae I and II may be formed with monovalent and divalent copper ions. Stable complexes are formed from one cupric ion with one or two molecules of a ligand of formula I or II and from one cuprous ion with two molecules of a ligand of formula I or II.

The copper complexes of isoquinoline and quinazoline derivatives of formula I are new substances and as such form a feature of the invention. The complexes with phenanthroline derivatives of formula II, in which $R_7$ and $R_{14}$ are the same or different and each represent a lower alkoxy or amino group and the other R-symbols are as hereinbefore defined, are new and as such form a feature of the invention.

The copper complexes of the compounds of formulae I and II are particularly active against *Mycoplasma gallisepticum*, the causative agent of chronic respiratory disease in poultry. Among the other mycoplasmas that are susceptible to the copper complexes, are *M. synoviae* (causing articular disease in poultry), *M. suipneumoniae* and *M. hyorhinis* (both affecting the respiratory tract of swine) and Spiroplasma citri (causing plant diseases). It has been found that the copper complexes of the invention are also effective against mycoplasma species that are resistant to tylosin and spectinomycin.

The complexes are suitably administered to animals in their food or drinking water or in a pharmaceutical composition, preferably for oral administration. The daily dosage will depend, e.g. on the causative agent and the species and age of the animal to be treated. For poultry a suitable dose is from 25 to 100 mg/kg body weight per day and for pigs from 10 to 25 mg/kg body weight per day. It is also possible to prevent mycoplasma infections in poultry by injecting the eggs with ca. 0.5 ml of a solution containing 1–5 g/l of the copper complex or by immersing the eggs in such a solution.

The invention includes within its scope animal feed compositions comprising a feed, which is preferably nutritionally balanced, containing at least one of the active copper complexes. The concentration of the active substance may be such that when the composition is fed to an animal, a therapeutically effective amount will be ingested. Alternatively feed concentrates may be used, i.e. feed compositions containing the active substance in a concentration higher than that normally used for treatment of mycoplasma infections. Such concentrates have to be mixed with an adequate amount of fodder to obtain the appropriate concentration in the fodder to be fed to the animals. A concentration of 0.1 to 10% by weight of the copper complex in the feed administered to the animal to be treated is suitably employed.

The invention also includes within its scope compositions comprising at least one active copper complex of the invention in association with a feed component or an inert mineral carrier. The concentration of copper complex in such compositions is also suitably between 0.1 and 10% by weight. Examples of feed components that may be used are ground grains, grain by products, animal protein substances, such as meat, and fish by-products; vitamin mixtures, e.g. vitamin A and D mixtures, riboflavin supplements and other vitamin B complexes, and bone meal, limestone, and other inorganic compounds to provide minerals.

The invention also includes pharmaceutical compositions comprising as the active ingredient, at least one of the copper complexes, in association with a pharmaceutically acceptable carrier or coating. Tablets and pills may be formulated in the usual manner with one or more pharmaceutically acceptable carriers, diluents or excipients, for example lactose, starch, microcrystalline cellulose (especially when direct compression is used) or highly purified silicon dioxide, and may include materials of a lubricating nature, for example calcium or magnesium stearate. Capsules made of soluble material, such as gelatin, may contain the active substance alone or in admixture with a solid or liquid diluent. Liquid preparations may be in the form of, e.g. suspensions, emulsions, syrups or elixirs of the active substance in water or another liquid medium commonly used for making orally acceptable pharmaceutical formulations such as liquid paraffin, or a syrup or elixir base. The active substance may also be made up in a form suitable for parenteral administration, i.e. as a sterile solution in water or an injectable organic solvent, or mixtures thereof, or as a suspension or emulsion in sterile water or an organic liquid usually employed for injectable preparations, for example a vegetable oil. The preparation may also be in a form suitable for inhalation, e.g. a liquid composition for administration as an aerosol or a solid composition as a dusting powder.

The antimycoplasma and other activities are also observed when a compound of formula I or II is used in association with a cupric salt. The invention accordingly includes within its scope compositions, which may be in solid or liquid form comprising at least one compound of formula I or II together with a cupric salt having an acceptable anion and, optionally, a suitable carrier or diluent. In aqueous media the cupric complexes are converted into cuprous complexes, as could be shown by spectrophotometric analysis. The cuprous complexes are lipophilic and may penetrate through the lipophilic membrane of mycoplasmas and exert their activity in the cell.

The copper complexes of the invention may also be used to combat mycoplasma infections in plants. Suitable solid or liquid formulations for the treatment of plants are well known to those skilled in the art. Compositions may comprise at least on copper complex according to the invention in association with a suitable carrier or diluent. Alternatively such compositions may contain at least one compound of formula I or II together with a cupric or cuprous salt with an acceptable anion in association with a suitable carrier or diluent.

Water-insoluble active compounds are conveniently formulated as dispersible powders and water-soluble active compounds as aqueous solutions. Compositions for use in the treatment of plants may include wetting agents and other materials of assistance in formulating the active compounds or in their use in plant therapy.

Plants may be treated, e.g. by spraying with a liquid composition or dispersible powder containing the active substance.

According to a feature of the invention the copper complexes of isoquinolines and quinazolines of general formula I and the novel copper complexes of phenanthroline derivatives as hereinbefore defined are prepared by contacting a solution of an appropriate copper salt with a solution of the isoquinoline, quinazoline or phenanthroline derivative in the same solvent, or in a solvent that is miscible with the solvent of the copper salt, and separating off the precipitate formed.

Suitable copper salts are the inorganic salts, especially the nitrates, which are easily soluble in various solvents. Examples of suitable solvents are acetone and acetonitrile, the latter being particularly suited for the preparation of cuprous complexes. Ethyl acetate is a suitable solvent when copper perchlorate complexes are to be prepared, ethanol is suitable for copper halides, methanol for copper sulphates and acetone is particularly suitable for copper nitrates.

For the preparation of complexes containing one copper ion with two ligand molecules, the copper salts should preferably be added to an excess of the ligand and the reverse procedure, using excess copper salt, is preferably applied when a complex of one copper ion with one ligand molecule is to be prepared. In the preparation of cupric complexes the copper salt solution is preferably slightly acidified in order to prevent hydrolysis. Only a small quantity of acid should be used as too much acid has an adverse effect on formation of the complex.

According to a further feature of the invention, cuprous complexes with an isoquinoline, quinazoline or phenanthroline derivative of formula I or II may be prepared by boiling an aqueous solution of the corresponding cupric complex. The cuprous complex is crystallized from the solution on cooling.

When a cuprous complex is to be prepared, it is preferred to carry out the reaction under an inert gas atmosphere and to use a freshly prepared copper salt.

It will be appreciated that the known copper complexes of phenanthroline derivatives of formula II may be prepared in a similar way to the novel complexes.

Within the group of compounds defined by general formula I, the isoquinolines and quinazolines of the general formula

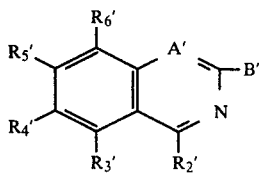

III wherein A', B', $R_1'$, $R_2'$, $R_3'$, $R_4'$, $R_5'$ and $R_6'$ are as hereinbefore defined for the symbols A, B, $R_1$, $R_2$, $R_3$, $R_4$, $R_5$ and $R_6$ respectively, with the proviso that when A' represents a —CH— group, B' represents a group of the formula Ia and $R_2'$ represents a hydrogen or halogen atom, then at least one of the symbols $R_1$ (in the group of formula Ia), $R_3'$, $R_4'$, $R_5'$ and $R_6'$ is other than hydrogen and that when B' represents a group of the formula Ia and $R_2'$ represents amino, then $R_1$ in the group of formula Ia represents a lower alkyl group, and their acid addition salts are new and as such form a feature of the invention. The compounds of formula III in which A' represents CH, B' represents 2-pyridyl, 6-methyl-2-pyridyl or 6-ethyl-2-pyridyl and $R_2'$ represents amino, methyl or ethyl and the other R-symbols represent hydrogen, are preferred in view of their biological activities or the activities of copper complexes derived from them. Particularly preferred are the compounds 1-ethyl-3-(2-pyridyl)isoquinoline,
1-methyl-3-(6-methyl-2-pyridyl)isoquinoline,
1-amino-3-(6-methyl-2-pyridyl)isoquinoline,
1-amino-3-(6-methyl-2-pyridyl)isoquinoline and
1-methyl-3-(2-pyridyl)isoquinoline and their acid addition salts.

Compounds in which $R_2'$ represents the amino group are specifically preferred as they can easily be synthesized.

In addition to antimycoplasma activity the new compounds of the invention and/or their mixtures with copper salts show other therapeutically useful activities, for instance against gram positive bacteria, fungi, yeasts, mycobacteria (including a multiresistent strain) and trichomonads. They may therefore be used in the treatment of various infections.

The compounds of formula III in which B' represents a group of the formula Ib and $R_2$ represents the amino group, particularly the quinazoline derivatives, and their acid addition salts, are useful as anti-hypertensive agents. Preferred compounds in this respect are 2-(1-methyl-1H-imidazole-2-yl)-4-quinazolinamine and 2-(1-ethenyl-1H-imidazole-2-yl)-4-quinazolinamine and their acid addition salts.

For the above purposes, the compounds, in association with a copper salt if desirable, are suitably administered in the form of pharmaceutical preparations as hereinbefore described. Suitable daily dosages of the coppercomplexes for adult humans will range from 50 to 200 mg p.o. and of the antihypertensive agents from 25 to 150 mg p.o.

According to a feature of the invention the novel isoquinoline and quinazoline derivatives of formula III wherein $R_2'$ represents a hydrogen, bromine or chlorine atom or a methyl, amino, lower alkylamino or di(lower alkyl) amino group, and the other symbols are as hereinbefore defined, are prepared by reacting a nitrile of the general formula:

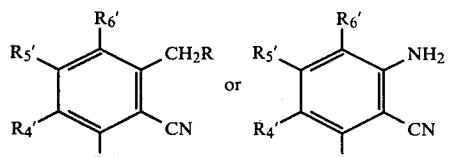

| IVa | IVb | wherein R, $R_3'$, $R_4'$, $R_5'$ and $R_6'$ are as hereinbefore defined, in the presence of a basic alkali metal compound, with a nitrile of the general formula B''—CH (V), in which B'' represents a group of the formula Ia or a group of the formula

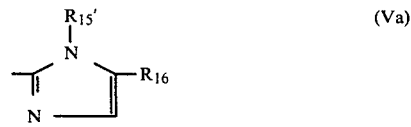

(Va)

in which R₁₅' represents a lower alkyl or lower alkenyl group or a protecting group and R₁₆ is as hereinbefore defined, hydrolyzing the product formed and removing, if desired, the group R₁₅' to obtain a 1-aminoisoquinoline or 4-aminoquinazoline derivative of the general formula

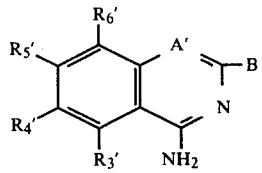

VI wherein the various symbols are as hereinbefore defined and converting, if desired, the amino group into a hydrogen atom or another substituent within the definition of $R_2'$.

Suitable protecting groups within the meaning of $R_{15}'$ are:
- toluene-p-sulfonyl, benzyloxymethyl or lower alkoxymethyl, which groups may be removed by hydrolysis;
- allyl, vinyl or propen-1-yl, which groups may be removed by oxydation, for instance with alkaline permanganate;
- benzyl, which may be removed by hydrogenation.

It is sometimes necessary to convert the allyl group into the prop-1-enyl group with the aid of a strong base, such as potassium t-butoxide.

Preferred basic alkali metal compounds are amides or dialkylamides, such as sodium or potassium amide or lithium (dialkyl) amide (e.g. lithium(dimethyl)amide).

When one or more of the symbols $R_3'$, $R_4'$, $R_5'$ and $R_6'$, represent bromine or iodine a primary amide, such as potassium amide, should preferably not be used, as in that case after substitution of the bromine or iodine substituent by an amino group an amidine may be formed.

The reaction between the nitriles of formulae IV and V is preferably carried out by keeping a mixture of the reactants in an inert organic solvent or, when the alkali metal compound is a primary amide, in liquid ammonia, under an inert gas atmosphere for several hours without heating. Suitable inert organic solvents are, for example, ethers such as diethyl ether or tetrahydrofuran.

When an amide, e.g. lithium(dimethyl)amide is used, it is suitably dissolved in an aprotic polar solvent, such as hexamethylphosphoric triamide (HMPTA). The reaction is preferably started at a low temperature, for example between $-50°$ and $-80°$ C., and continued at a temperature up to 60° C.

The starting materials of formulae IV and V are known compounds or can be prepared by methods known per se for the preparation of organic nitriles. By the term "methods known per se" as used in this specification is meant methods heretofore used or described in the chemical literature.

The conversion of the amino group in the compound of formula VI may be carried out as depicted in the following reaction scheme, in which $R_{17}$ represents a hydrogen atom or a lower alkyl group and $R_{18}$ represents a lower alkyl group, X represents chlorine or bromine and the other symbols are as hereinbefore defined.

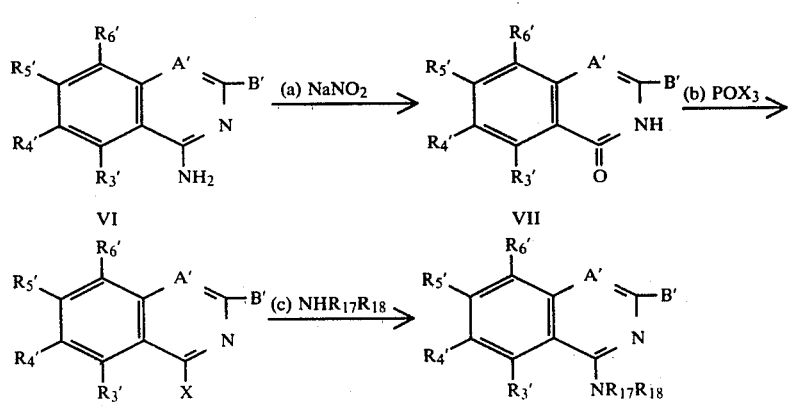

-continued

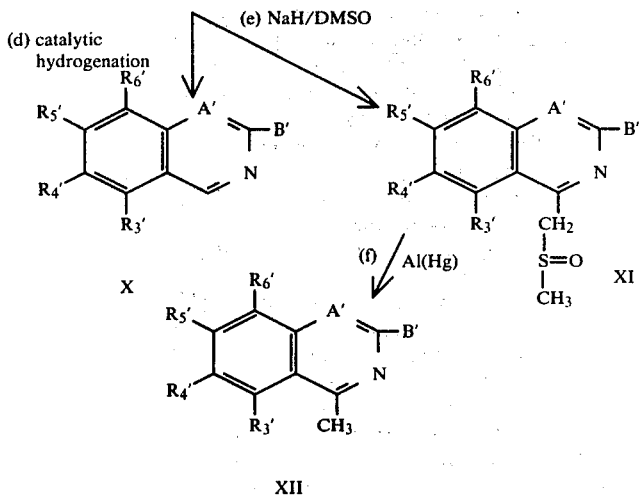

The processes to prepare certain compounds of formula III, indicated in the reaction scheme by (b), (c), (d) and (f) are further features of the present invention.

Reaction (a) is preferably carried out by adding dropwise a solution of sodium nitrite in water to a solution of the aminoisoquinoline or aminoquinazoline of formula VI in an organic solvent (e.g. glacial acetic acid), under cooling with ice, and then keeping the mixture at room temperature or refluxing it for a few hours.

Reaction (b) is preferably carried out by refluxing the hydrochloride of the compound of formula VII for a few hours in phosphorus oxychloride or phosphorus oxybromide.

Reaction (c) is preferably carried out by heating a solution of the compound of formula VIII in a lower alcohol (e.g. ethanol) at a temperature between 100 and 150° C. in a closed vessel (e.g. a Carius tube) with a large excess of the amine.

Reaction (d) is preferably carried out by catalytically hydrogenating the compound of formula VIII at room temperature in alcoholic (e.g. methanolic) solution in the presence of a base (e.g. sodium hydroxide), using, for example, palladium on carbon as the catalyst.

Reaction (e) is preferably carried out by stirring a suspension of sodium hydride in anhydrous dimethyl sulphoxide at an elevated temperature (e.g. 70° C.) for a few hours, adding dropwise with ice-cooling a solution of the compound of formula VIII in anhydrous tetrahydrofuran and subsequently stirring the reaction mixture for a few hours at elevated temperature (e.g. 50° C.).

Reaction (f) is preferably carried out by mixing freshly prepared aluminium amalgam with a solution of the 1-methylsulphinylmethylisoquinoline or 4-methylsulphinylmethylquinazoline of formula XI and refluxing the mixture for a short time, e.g. 30 minutes.

According to another feature of the invention the compounds of general formula III in which A' represents a CR group, B' represents a group of the formula Ia, $R_{2'}$ represents a lower alkyl or phenyl group and the other symbols are as hereinbefore defined, are prepared by reacting a compound of the general formula

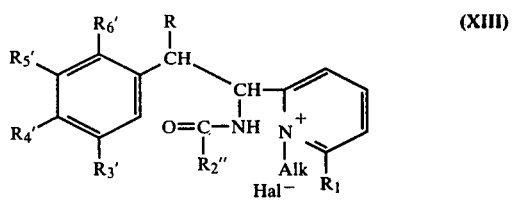

wherein Alk represents a lower alkyl group (preferably methyl), Hal⁻ represents a halogen (preferably chlorine, bromine or iodine) ion, $R_{2''}$ represents a lower alkyl or phenyl group and the other symbols are as hereinbefore defined, with phosphorus oxychloride under the conditions of the Bischler-Napieralksky reaction (i.e. heating the reactants in an inert solvent) and removing the N-alkyl group by a method known per se, e.g. by reaction with triphenylphosphine in dimethyl formamide. The reaction with phosphorus oxychloride is preferably carried out by refluxing the reactants in an inert organic solvent, such as toluene or xylene.

The starting materials of formula XIII may be obtained as indicated in the following reaction scheme:

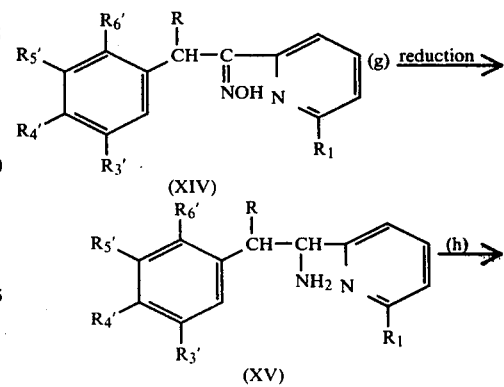

-continued

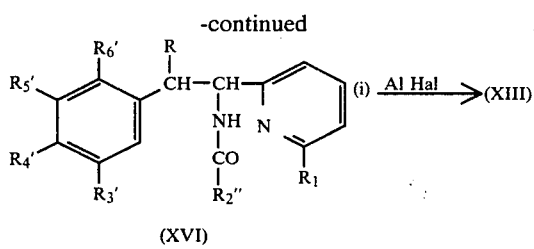

(XVI)

wherein the various symbols are as hereinbefore defined. The ketoxime of formula XIV may be prepared by the method described by E. Niemers and R. Hiltmann, Synth. 1976, 593 or by an analogous method.

The reduction step (g) may be carried out by reacting a solution of the ketoxime of formula XIV at elevated temperature (e.g. 80° C.) with zinc or zinc amalgam in the presence of a base (e.g. ammonia). Examples of suitable solvents are alcohols such as ethanol and mixtures of aqueous ammonia with ethanol.

Reaction (h) is suitably carried out by refluxing the reactants in an organic solvent. The amine of formula XV is reacted with a suitable reactive derivative, e.g. the acid anhydride or halide, or a lower alkyl ester of an acid of formula $R_{2''}COOH$. Suitable solvents are chloroform, carbon tetrachloride and benzene. When an acid chloride is used, the reaction is preferably carried out in the presence of a base such as triethylamine.

Reactions (g) and (h) may also be carried out in a single step, provided that an acid halide is not used, as this may react directly with the ketoxime. In this combined reaction when the acid $R_{2''}COOH$ is an alkyl carboxylic acid in which the alkyl moiety contains from 1 to 4 carbon atoms, the acid may also be used as solvent.

The quaternization (i) is suitably carried out by refluxing the alkyl halide and compound of formula XVI in acetone.

According to another feature of the invention, compounds of formula III in which B' represents a group Ib with unsubstituted nitrogen atom ($R_{15}$=hydrogen) and the other symbols are as hereinbefore defined, are prepared by removing the N-substituent from a corresponding N-substituted compound. Suitable N-substituents are those mentioned as protecting groups within the definition of $R_{15}'$. They may be removed by methods hereinbefore described.

Suitable acid addition salts of the compounds of formula III are the non-toxic salt, which implies that they are not harmful to the animal organism when used in therapeutic doses. Such acid addition salts may be derived from inorganic acids, such as the hydrohalic acids (e.g. hydrochloric and hydrobromic acid) and sulphuric acid, and organic acids such as oxalic, maleic, tartaric, citric, acetic, lactic, succinic, fumaric and pamoic acid. The acid addition salts may be prepared by methods known per se, for example by treating the base with the equivalent amount of the acid in an inert solvent.

The compounds of formula III and their non-toxic acid addition salts are suitably administered in a pharmaceutical composition as hereinbefore described with respect to the copper complexes. Such compositions are a further feature of the invention.

Known isoquinolines within the scope of formula I may also be prepared by the processes hereinbefore described for the preparation of isoquinolines of formula III. The phenanthrolines of formula II may be prepared by the application or adaptation of methods known per se.

The following tables show some activities—expressed as minimum inhibiting concentration (MIC)—of the prepared compounds against various microorganisms. The compounds are identified by reference to the Example in which they are described. When more than one compound is mentioned in an Example, they are distinguished by a number between parentheses, corresponding to their order of occurrence, for instance: VI (2) refers to the second compound prepared according to Example VI. The term "with Cu" refers to tests conducted in media containing 50 μg/ml $Cu^{2+}$.

TABLE I.

Activity against *Mycoplasma gallisepticum.*

| Compound of Example | MIC (μg/ml) | with Cu | Compound of Example | MIC (μg/ml) | with Cu |
|---|---|---|---|---|---|
| XIIc (1) | >100 | 0.4 | IIb | 6 | |
| XIIc (2) | | 0.06 | IIa | 1.5 | |
| XVa | >100 | 1.5 | IId | 12.5 | 25 |
| XVIa | 25 | 0.2 | IIe | 25 | |
| XVIIc | >100 | 0.2 | IVa | 1.5 | |
| XVIIIa | >100 | 0.2 | V | 3 | |
| XIXb | >100 | 6 | IVb | 0.8 | |
| XXa | >100 | 3 | XIc | | 0.1 |
| VIIIa | 100 | 12.5 | XIIId | | 0.06 |
| VIIIb | 1.5 | 0.2 | XIIb | | 0.03 |
| VIIId | 1.5 | 0.2 | XIb | | 1 |
| XIIc (3) | 6 | 0.06 | XIVb | | 0.2 |
| IX (1) | 100 | 0.03 | VII | | 0.4 |
| VIIIc | 3 | 0.4 | VIIIi | | 0.2 |
| VIIIe | 100 | 0.06 | X | | 0.4 |
| VIIIh | >100 | 0.05 | XVb (1) | 12.5 | 0.8 |
| VIIIj | 100 | 0.2 | XVb (2) | 12.5 | 1.5 |
| VIIIf | >100 | 0.05 | XVb (3) | 12.5 | 1.5 |
| VIIIg | 100 | 0.06 | XVIb (1) | 6 | 0.2 |
| VI (1) | 0.4 | | XVIb (2) | 6 | 0.4 |
| III | 0.2 | | XVIb (3) | 12.5 | 0.2 |
| I | 0.2 | 0.03 | XVIId (1) | 25 | 0.2 |
| IIc | 3 | 0.4 | XVIId (2) | 12.5 | 0.2 |
| XVIId (3) | 12.5 | 0.2 | VI (2) | 0.8 | |
| XVIIIb (1) | 12.5 | 0.2 | IVc | 0.8 | |
| XVIIIb (2) | 6 | 0.2 | IIf | | 0.03 |
| XVIIIb (3) | 12.5 | 0.2 | IX (2) | | 0.02 |
| XIXb (2) | 50 | 3 | VIIIk | | 0.2 |
| XIXb (3) | 50 | 3 | VIIIl | | 0.2 |
| XXb (2) | 25 | 1.5 | XIIIf | | 0.03 |
| XXb (3) | 50 | 6 | | | |

TABLE II.

Activities against other Mycoplasma species.

| | MIC (μg/ml) | | | | | | |
|---|---|---|---|---|---|---|---|
| | with Cu | | | | | | |
| Compound of Example | IX(2) | IX(1) | VIIIe | XIIb | VI(1) | III | I |
| *M. synoviae* | 0.05 | 0.025 | 0.1 | 0.1 | | 3 | 1 |
| *M. meleagridis* | 0.013 | 0.025 | 0.05 | 0.05 | | | |
| *M. suipneumoniae* | | | | | 3 | 1 | 1 |
| *M. hyorhinis* | | | | | 3 | 3 | 1 |
| *M. Hyorhinis* (tylosin resistent) | | | | | 1 | 1 | 1 |
| *M. hyorhinis* | | | | | | 1 | 0.3 |

TABLE II.-continued

Activities against other Mycoplasma species.

| Compound of Example | MIC (μg/ml) with Cu | | | | | | |
|---|---|---|---|---|---|---|---|
| | IX(2) | IX(1) | VIIIe | XIIb | VI(1) | III | I |
| (spectinomycin resistent) | | | | | | | |

TABLE III

| Activities against *Spiroplasma citri.* | | | |
|---|---|---|---|
| Compound of Example | MIC (μg/ml) with Cu | Compound of Example | MIC (μg/ml) with Cu |
| VI (1) | 50 | VIIIh | 0.4 |
| I | 25 | VIIIf | 0.4 |
| IIf | 25 | VIIIg | 0.8 |
| XIIc (1) | 0.2 | IX (2) | 0.2 |
| XII (3) | 0.2 | XIIId | 0.2 |
| IX | 0.4 | XIIb | 0.05 |
| VIIIe | 0.1 | | |

The activities of the following compounds, not mentioned in the Examples, were also measured.

TABLE IVa

| Compound | Formula | Meaning of symbols (symbols not mentioned are hydrogen) |
|---|---|---|
| A | II | $R_7 = R_{14} = CH_3$ |
| B | I | $A = N, B = 2$-pyridyl |
| C | I | $A = N, B = 2$-pyridyl, $R_4 = Cl$ |
| D | I | $A = C(C_{11}H_{23}), B = 2$-pyridyl |
| E | II | $R_7 = R_{14} = NH_2$ |
| F | II | $R_7 = NH_2$ |
| G | II | $R_7 = CH_3O$ |
| H | II | $R_7 = R_{14} = CH_3O$ |
| I | II | $R_7 = CH_3$ |

TABLE IVb

Activities against *M. gallisepticum* and *Spiroplasma citri.*

| | MIC (μg/ml) | |
|---|---|---|
| Compound | M. gall. with Cu | S.Citri (with Cu) |
| A | | 0.03 |
| B | 0.5 | |
| C | 0.8 | |
| D | | 0.8 |
| E | 50 | 0.8 |
| F | 25 | 0.8 |
| G | >100 | 3 |
| H | | 1.5 |
| I | | 0.2 |

It was investigated whether M. gallisepticum K514 develops a resistance against the compounds of Examples IX (1), IX (2), VIIIe and XIIb in the presence of copper ions. The MIC's in the presence of 100 μg/ml $Cu^{2+}$ were determined in the usual way. The test tubes containing the highest concentration of each compound in which a considerable growth of micro-organism still occurred, were used for inoculation in a next determination. This procedure was repeated 12 times without a significant increase of the MIC's. Consequently, no resistance is developed.

It could be observed that also the activities of the complex compounds increase when some copper salt is added to the liquid. This might be an indication that the copper complexes partly dissociate in solution.

The following Examples illustrate the preparation of copper complexes of compounds of formulae I and II and of compounds of formula I (including novel compounds of formula III) according to the invention. In the Examples infra red absorption maxima are given in $cm^{-1}$. The structures of the copper complexes were confirmed by elemental analysis and IR spectra. The structures of the compounds of formula I were confirmed by IR, NMR and mass spectra.

EXAMPLE I

To a freshly prepared solution of 314 mg (0.00250 mole) of cuprous nitrate in ca. 100 ml of acetonitrile, a clear solution of 1.04 g (0.00500 mole) of 2,9-dimethyl-1,10-phenanthroline in ca. 100 ml of acetonitrile was added dropwise with vigorous stirring and under a nitrogen atmosphere. After the reaction mixture had been allowed to stand for about one hour, the deep red precipitate of bis(2,9-dimethyl-1,10-phenanthroline)cuprous nitrate was filtered off and crystallized from water.

| Analysis: | | |
|---|---|---|
| | Calculated | Found |
| C: | 62.04% | 61.44/61.66% |
| H: | 4.46% | 4.63/4.62% |
| Cu: | 11.72% | 11.68/11.51% |
| N: | 12.92% | 12.82% |
| O: | 8.86% | 9.29/9.46% |

Infra red spectrum (hereinafter abbreviated to "IR"): 850, 1335, 1380, 1493, 2585.

EXAMPLE II

Proceeding as described in Example I, but substituting the appropriate phenanthroline or isoquinoline derivative for the 2,9-dimethyl-1,10-phenanthroline the following compounds were prepared.

(a) Bis[1-amino-5-chloro-3-(2-pyridyl)isoquinoline]cuprous nitrate.

IR: 780, 795, 960, 1328, 1360, 1380, 1467, 1490, 1545, 1590, 1605.

On admixing the reactants a deep red solution was obtained, from which a small amount of green material precipitated. After filtration, the solution was concentrated by removal of most of the solvent and the red-brown precipitate obtained was filtered off.

(b) Bis[1-amino-7-methyl-3-(2-pyridyl)isoquinoline]cuprous nitrate.

The product was not recrystallized.

| Analysis: | | |
|---|---|---|
| | Calculated | Found |
| C: | 60.44% | 60.02/59.99% |
| H: | 4.40% | 4.66/4.57 |
| Cu: | 10.66% | 10.60/10.70% |
| N: | 16.45% | 16.38% |
| O: | 8.05% | 8.68/8.67 |

IR: 777, 800, 842, 1327, 1380, 1445, 1510, 1560, 1618, 3190, 3330, 3430.

(c) Bis[1-amino-3-(2-pyridyl)isoquinoline]cuprous nitrate.

The product was not recrystallized.

| Analysis: | Calculated | Found |
|---|---|---|
| C: | 59.20% | 59.12/59.11% |
| H: | 3.90% | 4.29/4.13% |
| Cu: | 11.18% | 11.13/11.12% |
| N: | 17.26% | 17.13% |
| O: | 8.54% | 8.88/8.90% |

IR: 737, 780, 790, 1320, 1380, 1440, 1470, 1500, 1560, 1597, 1615, 3180, 3300, 3430.

(d) Bis(1,10-phenanthroline)cuprous nitrate.
The product was not recrystallized.

| Analysis: | Calculated | Found |
|---|---|---|
| C: | 59.31% | 59.34% |
| H: | 3.32% | 3.33% |
| Cu: | 13.08% | 13.08/13.03% |
| N: | 14.41% | 14.31% |
| O: | 9.88% | 10.07% |

IR: 717, 838, 1338, 1380, 1422, 1500, 1628.

(e) Bis(2,9-dichloro-1,10-phenanthroline)cuprous nitrate.
The product was not recrystallized.

| Analysis: | Calculated | Found |
|---|---|---|
| C: | 46.21% | 46.08/46.16% |
| H: | 1.94% | 2.27/2.12% |
| Cl: | 22.73% | 22.79% |
| Cu: | 10.19% | 10.13/9.99% |
| N: | 11.20% | 11.29% |
| O: | 7.70% | 8.08/8.19% |

IR: 852, 908, 1085, 1130, 1145, 1340, 1370, 1380, 1410, 1478, 1560.

(f) Bis[1-amino-3-(6-methyl-2-pyridyl)isoquinoline]cuprous nitrate.
The product was not recrystallized.

| Analysis: | Calculated | Found |
|---|---|---|
| C: | 60.44% | 60.32% |
| H: | 4.40% | 4.50% |
| Cu: | 10.66% | 10.52% |
| N: | 16.45% | 16.32% |
| O: | 8.05% | 8.21% |

IR: 3420, 3300, 3170, 1620 1605, 1565, 1503, 1470, 1438, 1383, 1320, 1262, 1250, 1238, 1162, 1030, 952, 795, 735, 680, 585, 495.

EXAMPLE III

A solution of 1.04 g (0.005 mole) of 2,9-dimethyl-1,10-phenanthroline in ca. 150 ml of acetone was added dropwise with stirring to a clear solution of 7.24 g (0.03 mole) of cupric nitrate trihydrate to which a few drops of dilute nitric acid were added. The precipitate formed, consisting of mono(2,9-dimethyl-1,10phenanthroline)-cupric nitrate was filtered off and washed with acetone,

| Analysis: | Calculated | Found |
|---|---|---|
| C: | 42.48% | 42.41% |
| H: | 3.06% | 3.12% |
| Cu: | 16.85% | 16.15/16.27% |
| N: | 14.16% | 14.13% |
| O: | 24.25% | 24.16% |

IR: 725, 863, 1000, 1015, 1270, 1360, 1380, 1495, 1592.

EXAMPLE IV

Proceeding as described in Example III, but substituting the appropriate isoquinoline derivative for the 2,9-dimethyl-1,10-phenanthroline, the following compounds were prepared.

(a) Mono[1-amino-3-(2-pyridyl)isoquinoline]cupric nitrate.

| Analysis: | Calculated | Found |
|---|---|---|
| C: | 41.13% | 41.24% |
| H: | 2.71% | 2.80% |
| Cu: | 15.54% | 15.58/15.24% |
| N: | 17.13% | 17.05% |
| O: | 23.48% | 23.41% |

IR: 737, 757, 780, 790, 995, 1010, 1275, 1380, 1445, 1475, 1505, 1563, 1640, 3360, 3480.

(b) Mono[1-amino-5-chloro-3-(2-pyridyl)isoquinoline]cupric nitrate.

| Analysis: | Calculated | Found |
|---|---|---|
| C: | 37.93% | 38.10% |
| H: | 2.27% | 2.43% |
| Cl: | 8.00% | 7.84% |
| Cu: | 14.33% | 14.06/14.28% |
| N: | 15.80% | 15.83% |
| O: | 21.66% | 21.69% |

IR: 788, 800, 965, 1000, 1275, 1360, 1380, 1490, 1548, 1595, 1618, 3360, 3480.

(c) Mono[1-amino-3-(6-methyl-2-pyridyl)isoquinoline]cupric nitrate.

| Analysis: | Calculated | Found |
|---|---|---|
| C: | 42.60% | 42.84% |
| H: | 3.10% | 3.32% |
| Cu: | 15.03% | 14.96% |
| N: | 16.57% | 16.26% |
| O: | 22.70% | 22.00% |

IR: 3480, 3380, 3260, 1640, 1605, 1565, 1505, 1480, 1440, 1382, 1297, 1270, 1168, 1028, 1010, 843, 798, 763, 750, 731, 678, 590, 495.

EXAMPLE V

A clear solution of 1.218 g (0.005 mol) of cupric nitrate trihydrate in ca. 200 ml of acetone (to which a few drops of dilute nitric acid were added) was slowly added dropwise and with stirring to a solution of 6.64 g (0.03 mol) of 1-amino-3-(2-pyridyl)isoquinoline in ca. 300 ml of acetone. The precipitate formed, consisting of bis[1-amino-3-(2-pyridyl)isoquinoline]cupric nitrate, was filtered off and washed with acetone.

Analysis:

|    | Calculated | Found       |
|----|------------|-------------|
| C: | 53.37%     | 53.42/53.38%|
| H: | 3.52%      | 3.80/3.80%  |
| Cu:| 10.08%     | 9.71/9.63%  |
| N: | 17.79%     | 17.54/17.62%|
| O: | 15.24%     | 15.62/15.95%|

IR: 735, 760, 780, 792, 1015, 1330, 1380, 1445, 1482, 1500, 1563, 1645, 3220, 3320.

EXAMPLE VI

Proceeding as described in Example V but using 2,9-dimethyl-1,10-phenanthroline there was prepared bis(2,9-dimethyl-1,10phenanthroline)cupric nitrate monohydrate, melting point 236° C. (with decomposition).

Similarly, by using 1-amino-3-(6-methyl-2-pyridyl-)isoquinoline, there was prepared bis[1-amino-3-(6-methyl-2-pyridyl) isoquinoline]cupric nitrate.

Analysis:

|    | Calculated | Found  |
|----|------------|--------|
| C: | 54.75%     | 54.59% |
| H: | 3.98%      | 4.28%  |
| Cu:| 9.65%      | 9.01%  |
| N: | 17.03%     | 16.69% |
| O: | 14.59%     | 15.37% |

IR: 3460, 3340, 3200, 1640, 1620, 1603, 1565, 1508, 1473, 1458, 1382, 1330, 1282, 1165, 1015, 955, 882, 798, 750, 735, 675, 590, 490.

EXAMPLE VII

A solution of 15.15 g (0.1 mol) of 4-chloro-2-methylbenzonitrile in 40 ml of anhydrous tetrahydrofuran was added under a nitrogen atmosphere to a suspension of 0.2 mol of potassium amide in liquid ammonia at −33° C. After 10 minutes a solution of 15.7 g (0.15 mol) of 2-cyanopyridine in 60 ml of anhydrous tetrahydrofuran was added. The mixture was kept overnight (ca. 16 hours), during which time the ammonia evaporated, and it was then hydrolyzed with 200 ml of water. The tetrahydrofuran was subsequently distilled off and the aqueous residue was extracted with chloroform. After evaporation of the chloroform the crude product was sublimed at 220°–250° C. The sublimate was crystallized from chloroform, dissolved in diethyl ether and converted into the hydrochloride by addition of an ethereal solution of hydrogen chloride. The precipitate obtained was filtered off and twice crystallized from ethanol, to yield 1-amino-6-chloro-3-(2-pyridyl)isoquinoline hydrochloride, melting point 243° C.

EXAMPLE VIII

Using the method of Example VII, but substituting the appropriate substituted 2-methylbenzonitrile for the 4-chloro-2-methylbenzonitrile, the following compounds of formula I, in which A represents CH, B represents the 2-pyridyl group and $R_2$ represents an amino group, were prepared.

|     | $R_3$ | $R_4$  | $R_5$       | $R_6$ | m.p. hydrochloride (°C.) | cryst. solvent* |
|-----|-------|--------|-------------|-------|--------------------------|-----------------|
| a   | H     | $CH_3O$| $CH_3O$     | H     | 275.5–276                | $CH_3OH$        |
| b   | H     | H      | H           | $CH_3$| 281.7–285.4              | $C_2H_5OH$      |
| c   | H     | H      | $CH_3$      | H     | 277–278                  | $CH_3OH$        |
| d   | H     | $CH_3$ | H           | H     | 272–287                  | IPA/water       |
| e   | $CH_3$| H      | H           | H     | 274                      | IPA/water       |
| f   | $C_2H_5$| H    | H           | H     | 247                      | IPA/water       |
| g   | H     | H      | $n-C_{10}H_{21}$| H | 178.7–187.3              | IPA/water       |
| h   | H     | H      | H           | Cl    | 190                      | IPA/water       |
| i   | H     | Cl     | H           | H     | 253                      | $C_2H_5OH$/water|
| j   | Cl    | H      | H           | H     | 150.8–152.8              | IPA/water       |
| k   | H     | $C_2H_5$| H          | H     | 261°                     | $C_2H_5OH$      |
| l   | H     | I      | H           | H     | 240°                     | IPA             |

*IPA = isopropyl alcohol

EXAMPLE IX

Using the method of Example VII, but substituting 2-cyano-6-methylpyridine for the 2-cyanopyridine and 2-methylbenzonitrile for the 4-chloro-2-methylbenzonitrile, there was obtained 1-amino-3-(6-methyl-2-pyridyl)-isoquinoline hydrochloride. The compound was crystallized from isopropyl alcohol. Melting point 263.5°–264.5° C.

Similarly, starting from 2-cyano-6-ethylpyridine and 2-methylbenzonitrile, there was prepared 1-amino-3-(6-ethyl-2-pyridyl) isoquinoline hydrochloride. The compound was crystallized from ethanol. Melting point 251°–253° C.

EXAMPLE X

To a solution of 10.5 g (0.23 mol) of dimethylamine in 80 ml of tetrahydrofuran, 100 ml of 15% (w/v) n-butyl lithium in hexane (0.23 mol) were added under a nitrogen atmosphere. After 30 minutes, 18 g (0.1 mol) of hexamethylphosphoric triamide (HMPTA) were added, after which the mixture was cooled to −78° C. To the light-yellow solution obtained, 19.6 g (0.1 mol) of 4-bromo-2-methylbenzonitrile in 60 ml of anhydrous tetrahydrofuran were added in the course of 10 minutes, after which the deep red solution was stirred for another 15 minutes. Subsequently 15.7 g (0.15 mol) of 2-cyanopyridine in 60 ml of anhydrous tetrahydrofuran was added dropwise in the course of 10 minutes. The reaction mixture was heated to 60° C. for one hour and it was then hydrolysed with 400 ml of 10% (w/v) hydrochloric acid. The yellow precipitate obtained was filtered off, the filtrate was washed with diethyl ether, neutralised with sodium hydroxide and extracted with chloroform. The solvent was distilled off from the extract and the residue was sublimed. The product obtained was converted into the hydrochloride, as described in Example VII, and the hydrochloride was combined with the yellow precipitate and crystallised from ethanol. 1-Amino-6-bromo-3-(2-pyridyl)isoquinoline hydrochloride was obtained, melting point 257.5° C.

EXAMPLE XI (a) 28.11 g of a mixture of 1-amino-3-(6-methyl-2-pyridyl)isoquinoline (68%) and 1-amino-3-(2-methylphenyl)isoquinoline* (32%) was dissolved in 300 ml of glacial acetic acid and a solution of 44.8 g of sodium nitrite in water was added dropwise to the mixture cooled externally with ice. The reaction mixture was allowed to stand overnight and was then gently refluxed for one hour. The mixture was poured into water and extracted with chloroform. The chloroform was distilled off from the extract and ethereal hydrogen chloride was added to the residue. The precipitate obtained was filtered off and crystallised from ethanol.

*[In the preparation of 1-amino-3-(6-methyl-2-pyridyl)isoquinoline used as starting material, 1-amino-3-(2-methylphenyl)isoquinoline is obtained as a by-product. The corresponding isoquinolones can be separated more easily than the isoquinolines (as the 6-methyl-2-pyridyl derivative forms a hydrochloride and the 2-methylphenyl derivative does not). The mixture of isoquinolines was therefore used as the starting material.]

3-(6-Methyl-2-pyridyl)-1(2H)-isoquinolone hydrochloride was obtained. Melting point 131° C. (decomp.).

The free base, crystallised from a mixture of chloroform and petroleum ether (boiling range 40°-60° C.) melted at 160.5° C.

(b) 14.5 g of 3-(6-methyl-2-pyridyl)-1(2H)-isoquinolone hydrochloride [prepared as described in (a)] was refluxed for 4 hours in phosphorus oxychloride. The reaction mixture was poured onto ice and neutralised with aqueous sodium hydroxide. The crude product was filtered off and crystallised from ethanol.

1-Chloro-3-(6-methyl-2-pyridyl)isoquinoline was obtained, melting point 140.3°-140° C. 1 g of the base was converted into the hydrochloride (as described in Example VII), which was twice crystallised from isopropyl alcohol, to obtain a pure product, melting point 142.5°-143.5° C.

(c) 20 g of 1-chloro-3-(6-methyl-2-pyridyl)isoquinoline, a solution of 1 g of sodium hydroxide dissolved in 4 ml of water and 1 g of 10% w/w palladium on charcoal were taken up in 150 ml of methanol. The mixture was stirred for 6 hours at room temperature under a hydrogen atmosphere at normal atmospheric pressure. The crystals of the starting material gradually dissolved. The reaction mixture was filtered and the solvent evaporated. The residue was taken up in chloroform and washed with water. The chloroform was evaporated and the crude residue was purified by column chromatography, using a silica gel column and a mixture of petroleum ether (boiling range 40°-60° C.), dichloromethane and methanol (90:5:5) as the eluent to yield a light yellow oil, consisting of 3-(6-methyl-2-pyridyl)isoquinoline. The base was converted into its hydrochloride which, after crystallisation from isopropyl alcohol, melted at 157° C.

EXAMPLE XII (a) A suspension of 6 g of sodium hydride (55–60% in paraffin) in 80 ml of anhydrous dimethyl sulphoxide was stirred for 2 hours at 70° C. A solution of 8.8 g of 1-chloro-3-(6-methyl-2-pyridyl)isoquinoline (prepared as described in Example XI) in anhydrous tetrahydrofuran was added dropwise to the mixture with ice-cooling, to obtain a deep red-coloured reaction mixture. The mixture was stirred for 2 hours at 50° C. and was then extracted with dichloromethane, after addition of ice-water. The organic layer was washed with a saturated aqueous sodium chloride solution and with water and the solvent was then distilled off. The residue was dissolved in diethyl ether and ethereal hydrogen chloride was added to the solution. The precipitate obtained was filtered off and dissolved in water. The solution was made alkaline with aqueous sodium hydroxide and extracted with diethyl ether. The ether was distilled off and the residue was crystallised from a mixture of ethanol and pentane. 3-(-6-Methyl-2-pyridyl)-1-methylsulphinylmethylisoquinoline was obtained, melting point 198.0°-198.5° C. A portion of the base was converted into the hydrochloride which, after crystallisation from isopropyl alcohol, melted at 120°-121° C. (decomp.).

(b) 2.50 g of the product prepared as in (a) above (free base) was dissolved in 90 ml of tetrahydrofuran and 10 ml of water and 2 g of freshly prepared aluminium amalgam were added. The mixture was stirred for 10 minutes and was then refluxed for 30 minutes. The reaction mixture was filtered, the residue washed with tetrahydrofuran and the combined filtrate and washings concentrated. The crude residue was taken up in chloroform, the solution washed with water and the solvent distilled off. The residue was sublimed and the product obtained was further purified by column chromatography on silica gel using a mixture of petroleum ether (boiling range 40°-60° C.) and methanol (95:5) as the eluent. The oily product, 1-methyl-3(6-methyl-2-pyridyl)isoquinoline, was converted into its hydrochloride, which after crystallisation from a mixture of methyl isobutylketone and petroleum ether (boiling range 40°-60° C.), melted at 167.0° C.

(c) By proceeding as described in Example VII but replacing the 4-chloro-2-methylbenzonitrile by 2-methylbenzonitrile, there was prepared 1-amino-3-(2-pyridyl)isoquinoline. By proceeding as described in Example XI(a) and XI(b), but replacing the mixture of 1-amino-3-(6-methyl-2-pyridyl)isoquinoline and 1-amino-3-(2-methylphenyl)isoquinoline used as starting material by 1-amino-3-(2-pyridyl)isoquinoline, there was prepared 1-chloro-3-(2-pyridyl)isoquinoline. By proceeding as described in Example XII(a) and XII(b), but replacing, the 1-chloro-3-(6-methyl-2-pyridyl)isoquinoline by 1-chloro-3-(2-pyridyl)isoquinoline there was prepared 1-methyl-3-(2-pyridyl)isoquinoline. The product was converted into its hydrochloride which, after crystallisation from a mixture of isopropyl alcohol and petroleum ether (boiling range 40°-60° C.), melted at 156°-157° C.

EXAMPLE XIII (a) To a solution of 42.4 g (0.2 mol) of benzyl-2-pyridylketoxime (E. Niemers and R. Hiltmann, Synth. 1976, 593), 2 g of sodium hydroxide and 0.2 g of mercuric chloride in 300 ml of propionic acid and 100 ml of propionic acid anhydride, were added 52.4 g (0.8 mol) of zinc powder with stirring in portions of 0.5 g in the course of one hour. The solution became warm and turned purple. Stirring was continued at 80° C. until the purple colour turned to yellow (ca. 3 hours). The reaction mixture was cooled and filtered. The residue was thoroughly washed with water and then with chloroform and the chloroform solution obtained was successively washed with water, aqueous sodium bicarbonate and again with water. The solvent was distilled off and the residue was sublimed. The oily product was crystallised from a mixture of ethanol and petroleum ether (boiling range 60°-80° C.). N-[2-phenyl-1-(2-pyridyl)ethyl]propionamide was obtained as a white solid, melting point 91°-93° C.

(b) 27.85 g of the product, prepared as described in (a), were dissolved in 200 ml of acetone and to this solution 100 g (0.7 mol) of methyl iodide were added.

The reaction mixture was refluxed for 6 hours and was then concentrated by evaporation of the solvent. The NMR spectrum of the crude residue showed the characteristics of an amide with a quaternized pyridine ring. The product, N-methyl-2-(1-propionamido-2-phenylethyl)pyridinium iodide, was used in the next reaction step without further purification.

(c) The crude product, prepared as described in (b), was mixed with 300 ml of anhydrous toluene, and 100 ml of phosphorus oxychloride were added dropwise to the mixture. The temperature of the reaction mixture rose and the oil dissolved. The solution was refluxed for 4 hours and then toluene and phosphorus oxychloride were distilled off. The red-brown residue was poured into ice-water, and the aqueous solution was neutralised with sodium hydroxide and extracted five times with chloroform. The combined extracts were washed with water and then concentrated to obtain an oil.

The oily residue was dissolved in chloroform and made to crystallise by addition of acetone. The solid obtained was filtered off and crystallised from a mixture of acetone and chloroform. N-methyl-2-(1-ethyl-3-isoquinolyl)pyridinium iodide was obtained, melting point 172° C.

(d) A solution of 4 g of the product prepared in (c) and 14.4 g of triphenylphosphine in 100 ml of dimethyl formamide was refluxed for 16 hours. The solvent was then distilled off and the residue was dissolved in chloroform and extracted with water. The chloroform phase was concentrated and to the residue, hydrochloric acid and chloroform were added. The aqueous phase was separated off, neutralised with aqueous sodium hydroxide and extracted with chloroform. The extract was concentrated and the residue was sublimed to yield 1-ethyl-3-(2-pyridyl)isoquinoline as a light yellow oil. The base was converted into the hydrochloride, which after two crystallisations from isopropyl alcohol melted at 160.0°–160.5° C.

(e) By proceeding as described in Example XIII(a), (b), (c) and (d), but replacing the propionic acid and propionic anhydride used in step (a) by acetic acid and acetic anhydride there was prepared 1-methyl-3-(2-pyridyl)-isoquinoline (cf. Example XII(c)).

(f) Similarly, by using in step (a) butyric acid and butyric anhydride, there was prepared 1-propyl-3-(2-pyridyl)isoquinoline hydrochloride. The compound was crystallized from a mixture of ethanol and petroleum ether (boiling range 40°–60° C.). Melting point 155° C.

EXAMPLE XIV (a) 40 g (0.019 mol) of benzyl-2-pyridyl ketoxime was dissolved in 1 l of a concentrated (ca. 28% w/v) aqueous ammonia solution. To this solution were added 60 g of zinc powder, 8 g of ammonium acetate and 200 ml of ethanol and the mixture was refluxed for 4 hours. The reaction mixture was cooled and filtered and the residue washed with toluene. The filtrate was extracted three times with diethyl ether, after which 40 ml of 50% aqueous sodium hydroxide were added and the filtrate again extracted twice with diethyl ether. The combined extracts were washed with water to neutrality and the solvent distilled off. The residue was distilled at 100°–120° C./0.2 mmHg, to yield the corresponding amine, 2-phenyl-1-(2-pyridyl)ethylamine as a colourless liquid.

(b) The amine prepared as described in (a) was dissolved in chloroform and equivalent amounts of benzoyl chloride and triethylamine were added. The reaction mixture was refluxed for two hours and then washed with water and dried with sodium sulphate. The solvent was distilled off and the residue crystallised from ethanol to yield N-[2-phenyl-1-(2-pyridyl)ethyl]-benzamide.

By proceeding as described in Example XIII(b), (c) and (d) but replacing the N-[2-phenyl-1-(2-pyridyl)ethyl]propionamide used as starting material in Example XIII(b) by N-[2-phenyl-1-(2-pyridyl)ethyl]benzamide there was prepared 1-phenyl-3-(2-pyridyl)isoquinoline. The product was converted into its hydrochloride which melted at 153°–154° C.

EXAMPLE XV a. At a temperature of −40° C., 2 g (0.05 at) of potassium were added in small pieces and with stirring to 65 ml of liquid ammonia with such a speed that the blue coloration did not persist. Ferric nitrate was added as a catalist. To the solution of potassium in ammonia thus obtained, a solution of 3 g (0.025 mole) of 2-methylbenzonitrile in 10 ml of anhydrous diethyl ether were added dropwise at −40° C. After 5 minutes, a solution of 5 g (0.05 mole) of 1-methyl-1$\underline{H}$-imidazole-2-carbonitrile (see P. Fournari, Bull.Soc.Chim.Fr.1968, 2438–2446) in 15 ml of diethyl ether were added dropwise to the dark red mixture. The reaction mixture was stirred for another two hours at −40° C. and then the cooling means were removed and the ammonia was allowed to evaporate overnight. The next day the reaction mixture was decomposed with water, after which diethyl ether was added. The organic layer was separated off, washed with water and concentrated. The residue was dissolved in 2-propanol and ethereal hydrogen chloride was added until the mixture was acidic. The precipitate formed was filtered off and crystallized from ethanol. The dihydrochloride of 1-amino-3-(1-methyl-1$\underline{H}$-imidazole-2-yl)isoquinoline was obtained with melting point 272° C.

b. By using similar procedures as described in Examples I, III and V, the compound obtained was converted into the following complexes:

Bis[1-amino-3-(1-methyl-1$\underline{H}$-imidazole-2-yl)isoquinoline]cuprous nitrate,
 I.R.: 3320, 3180, 1625, 1570, 1545, 1500, 1475, 1430, 1374, 1162, 1110, 987, 952, 922, 835, 767, 750, 680, 595, 523.

mono[1-amino-3-(1-methyl-1$\underline{H}$-imidazole-2-yl)isoquinoline]cupric nitrate,
 I.R.: 3470, 3325, 3215, 1635, 1620, 1565, 1540, 1488, 1447, 1380, 1270, 1173, 990, 925, 835, 752, 720, 690, 670, 505.

Bis[1-amino-3-(1-methyl-1$\underline{H}$-imidazole-2-yl)isoquinoline]cupric nitrate.
 I.R.: 3300, 3170, 1622, 1565, 1538, 1505, 1480, 1447, 1373, 1285, 1170, 1013, 957, 925, 875, 830, 745, 722, 690, 670, 505.

EXAMPLE XVI

A solution of 5.9 g (0.05 mole) of 2-aminobenzonitrile in 25 ml of anhydrous diethyl ether was added dropwise at 25° C. to a phenyl lithium solution, prepared from 7.9 g (0.05 mole) of bromobenzene and 0.7 g (0.1 at) of lithium wire in 50 ml of anhydrous diethyl ether. After 10 minutes stirring, a solution of 5.4 g (0.05 mole) of 1-methyl-1$\underline{H}$-imidazole-2-carbonitrile in 15 ml of diethyl ether was added dropwise. The mixture was refluxed for 2 hours and it was then decomposed with water. The ethereal layer, which contained only little of the desired compound, was separated off and the precipitate, which did not dissolve in diethyl ether, was taken up in chloroform. The chloroform solution was washed with water and dried and the solvent was distilled off. The residue solidified on addition of diethylether and the solid base obtained was dissolved in 2-propanol and converted into the hydrochloride. The salt was crystallized from a mixture of ethanol and diethyl ether. The dihydrochloride of 4-amino-2-(1-methyl-1H-imidazole-2-yl)quinazoline was obtained with melting point 253° C.

b. By using similar procedures as described in Examples I, III and V, the compound obtained was converted into the following complexes:
Bis[4-amino-2-(1-methyl-1H-imidazole-2-yl)quinazoline]cuprous nitrate,
I.R.: 3420, 3310, 3180, 1617, 1592, 1570, 1500, 1470, 1445, 1428, 1379, 1282, 1167, 953, 928, 855, 830, 763, 742, 712, 673, 520.
Mono[4-amino-2-(1-methyl-1H-imidazole-2-yl)quinazoline]cupric nitrate,
I.R.: 3540, 3430, 1635, 1592, 1567, 1495, 1475, 1415, 1375, 1280, 1182, 1042, 935, 830, 767, 675, 660, 503, 420.
Bis[4-amino-2-(1-methyl-1H-imidazole-2-yl)quinazoline]cupric nitrate,
I.R.: 3420, 3320, 3130, 1645, 1575, 1550, 1500, 1482, 1453, 1430, 1375, 1320, 1280, 1233, 1165, 1130, 1035, 975, 938, 893, 794, 770, 745, 675, 613, 520.

EXAMPLE XVII a. 100 f of activated manganese dioxide and 43.7 g (0.35 mole) of 1-ethenyl-1H-imidazole-2-methanol(prepared as described in Chem.

Abstr. 49, P15976b(1954)) were added to one liter of anhydrous acetone. The reaction mixture was stirred for three days at room temperature and it was then filtered. The filtrate was concentrated by evaporation of the solvent. The residue solidified on addition of petroleum ether (boiling range 29°-40° C.) and the solid was purified by sublimation. 1-Ethenyl-1H-imidazole-2-carboxaldehyde was obtained, melting point 48°-51° C.

b. A solution of 48.8 g (0.4 mole) of the compound obtained in 80 ml of pyridine was added dropwise to a solution of 30 g (0.43 mole) of hydroxylamine hydrochloride in 160 ml of pyridine, while the temperature was maintained at 20° C. by cooling. The mixture was stirred for half an hour at room temperature and then the solvent was thoroughly distilled off. To the residue, 300 ml of acetic anhydride were carefully added at 0° C. (heat effect). The reaction mixture was refluxed for another 10 minutes and then the liquid was distilled off. The last traces of acetic anhydride were removed by twice adding and evaporating a small amount of xylene. The residue was extracted with about 1 liter of diethyl ether. The ether was distilled off and the residue was crystallized from a mixture of diethyl ether and petroleum ether (boiling range 40°-60° C.). 1-Ethenyl-1H-imidazole-2-carbonitrile was obtained with melting point 81.5° C.

c. A solution of 7 g (0.06 mole) of 2-methylbenzonitrile in 30 ml of anhydrous diethyl ether was added dropwise at −40° C. to a mixture of 0.12 mole of potassium amide in 150 ml of liquid ammonia. The reaction mixture was stirred for 5 minutes and then a solution of 10.7 g (0.09 mole) of the compound obtained as described under b. in 75 ml of diethyl ether and 25 ml of tetrahydrofuran was added dropwise at −40° to −50° C. The mixture was stirred for 3 hours at −50° C. and then the cooling means were removed and the ammonia was allowed to evaporate overnight. The next day, 100 ml of diethyl ether were added and the mixture was decomposed with water. The organic layer was separated off, washed with water, dried and concentrated.

The residue was dissolved in 2-propanol and the solution was acidified with ethereal hydrogen chloride. The precipitate was crystallized from a mixture of ethanol and diethyl ether. The dihydrochloride of 1-amino-3-(1-ethenyl-1H-imidazole-2-yl) isoquinoline was obtained, melting point 240° C.

d. By using similar procedures as described in Examples I, III and V, the compound obtained was converted into the following complexes:
Bis[1-amino-3-(1-ethenyl-1H-imidazole-2-yl)isoquinoline]cuprous nitrate,
I.R.: 3440, 3330, 3210, 1620, 1562, 1512, 1455, 1440, 1380, 1330, 1275, 1195, 1150, 1130, 905, 822, 740, 725, 665, 505.
Mono[1-amino-3-(1-ethenyl-1H-imidazole-2-yl)isoquinoline]cupric nitrate,
I.R.: 3480, 3370, 3160, 1643, 1622, 1567, 1525, 1495, 1475, 1455, 1425, 1378, 1288, 1270, 1202, 1168, 1151, 1007, 960, 922, 835, 803, 747, 670, 505.
Bis[1-amino-3-(1-ethenyl-1H-imidazole-2-yl)isoquinoline]cupric nitrate,
I.R.: 3330, 3180, 1645, 1620, 1563, 1525, 1473, 1380, 1280, 1201, 1153, 1013, 922, 833, 745, 670, 505.

EXAMPLE XVIII a. To a phenyl lithium solution, prepared from 15.8 g (0.1 mole) of bromobenzene and 1.4 g (0.2 at) of lithium wire in 125 ml of anhydrous diethyl ether, a solution of 11.8 g (0.1 mole) of 2-aminobenzonitrile in 50 ml of diethylether was added dropwise at 20° to 25° C. The mixture was stirred for 10 minutes at room temperature and then a solution of 12 g (0.1 mole) of 1-ethenyl-1H-imidazole-2-carbonitrile (see Example XVIIb) in 30 ml of anhydrous tetrahydrofuran was added dropwise. The reaction mixture was refluxed for 3 hours and it was then decomposed with water. The solid, which did not dissolve in diethyl ether, was filtered off and dried and it was converted in 2-propanol into the hydrochloride. The salt was crystallized from a mixture of ethanol and diethyl ether. The dihydrochloride of 4-amino-2-(1-ethenyl-1H-imidazole-2-yl)quinazoline was obtained, melting point 218° C.

b. By using similar procedures as described in Examples I, III and V, the compound obtained was converted into the following complexes:
Bis[4-amino-2-(1-ethenyl-1H-imidazole-2-yl)quinazoline]cuprous nitrate,
I.R.: 3420, 3320, 3180, 1635, 1615, 1573, 1500, 1475, 1430, 1380, 1298, 1280, 1150, 1135, 952, 928, 888, 765, 740, 673, 520.
Mono[4-amino-2-(1-ethenyl-1H-imidazole-2-yl)quinazoline]cupric nitrate,
I.R.: 3400, 3340, 3200, 1645, 1590, 1568, 1505, 1480, 1435, 1378, 1300, 1225, 1170, 1153, 935, 903, 830, 765, 738, 522.
Bis[4-amino-2-(1-ethenyl-1H-imidazole-2-yl)quinazoline]cupric nitrate,
I.R.: 3300, 3100, 1645, 1590, 1578, 1505, 1480, 1433, 1375, 1300, 1270, 1168, 1152, 1135, 962, 935, 903, 830, 765, 742, 670, 612, 522.

EXAMPLE XIX a. To a solution of 5.9 g of 1-amino-3-(1-ethenyl-1H-imidazole-2-yl) isoquinoline (see Example XVIIc) in 150 ml of pyridine and 150 ml of 0.5 N methanolic sodium hydroxide, 300 ml of a 4% aqueous potassium permanganate solution were added dropwise with stirring at 0° to 10° C. The mixture was stirred for 2 hours at room temperature and it was then filtered. To the filtrate, 40 ml of 2 N hydrochloric acid were added and subsequently the liquid was thoroughly distilled off. The residue was taken up in dilute hydrochloric acid, filtered and made alkaline with dilute ammonia. The precipitated base was filtered off and dried. The base was converted in 2-propanol into the hydrochloride, which was crystallized from a mixture of ethanol, methanol and diethyl ether. The dihydrochloride of 1-amino-3-(1H-imidazole-2-yl)isoquinoline was obtained with melting point 255° C.

b. By using similar procedures as described in Examples I, III and V, the compound obtained was converted into the following complexes:

Bis[1-amino-3-(1H-imidazole-2-yl)isoquinoline]cuprous nitrate,
I.R.: 3340, 3200, 1622, 1562, 1505, 1465, 1412, 1380, 1320, 1192, 1145, 1100, 1040, 990, 950, 912, 865, 835, 745, 670, 585, 508.

Mono[1-amino-3-(1H-imidazole-2-yl)isoquinoline]cupric nitrate,
I.R.: 3320, 3200, 1622, 1550, 1505, 1470, 1445, 1372, 1330, 1190, 1175, 1100, 1085, 993, 911, 873, 850, 847, 821, 742, 725, 670, 585, 505.

Bis[1-amino-3-(1H-imidazole-2-yl)isoquinoline]cupric nitrate,
I.R.: 3400, 3320, 3200, 1625, 1550, 1503, 1468, 1445, 1380, 1325, 1188, 1157, 1120, 1100, 1040, 985, 910, 873, 848, 835, 742, 725, 670, 580, 505.

EXAMPLE XX a. 4-Amino-2-(1-ethenyl-1H-imidazole-2-yl)quinazoline (see Example XVIIIa) was converted into 4-amino-2(1H-imidazole-2-yl)quinazoline dihydrochloride by the procedure described in Example XIXa. Melting point > 300° C.

b. By using similar procedures as described in Examples I, III and V, the compound obtained was converted into the following complexes:

Bis[4-amino-2-(1H-imidazole-2-yl)quinazoline]cuprous nitrate,
I.R.: 3430, 3190, 1625, 1568, 1500, 1475, 1423, 1380, 1300, 1288, 1152, 1115, 950, 930, 765, 670, 595, 522.

Mono[4-amino-2-(1H-imidazole-2-yl)quinazoline]cupric nitrate,
I.R.: 3300, 3160, 1630, 1580, 1490, 1370, 1150, 1110, 955, 940, 932, 820, 765, 743, 670.

Bis[4-amino-2-(1H-imidazole-2-yl)quinazoline]cupric nitrate,
I.R.: 3320, 3180, 1625, 1570, 1505, 1500, 1475, 1435, 1380, 1090, 920, 768, 747, 670.

EXAMPLE XXI

A solution of 5.9 g (0.05 mole) of 2-aminobenzonitrile in 25 ml of diethyl ether was added dropwise at 25° C. to a phenyl lithium solution, prepared from 7.8 g (0.05 mole) of bromobenzene and 0.7 g (0.1 at) of lithium wire in 50 ml of anhydrous diethyl ether. The mixture was stirred for 10 minutes and then a solution of 5.9 g (0.05 mole) of 6-methyl-2-pyridinecarbonitrile in 15 ml of diethyl ether were added dropwise. The reaction mixture was gently refluxed for 2 hours and it was then decomposed with water, after which so much chloroform was added that two clear layers were formed. The organic layer was separated off, washed with water and concentrated. The residue was crystallized from toluene. 2-(6-Methyl-2-pyridyl)-4-quinazolinamine was obtained, melting point 201° C.

I claim:

1. A method for combatting mycoplasma-induced diseases in animals, including humans, and plants, comprising treating the animal or plant with a composition containing a carrier acceptable for use for the subject being treated and an effective amount of either a complex of a copper salt, having an anion substantially harmless to the subject being treated with an organic compound of the formula

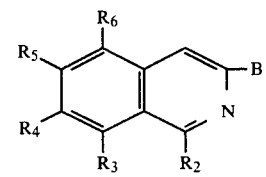

wherein B represents a group of the formula

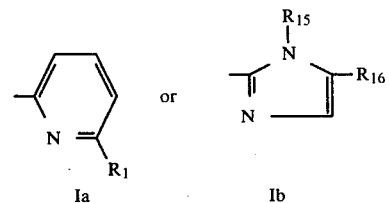

in which $R_1$ represents a hydrogen atom or a lower alkyl group, $R_{15}$ represents a hydrogen atom or a lower alkyl or lower alkenyl and $R_{16}$ represents a hydrogen atom or a nitro group, $R_2$ represents a hydrogen or halogen atom or a lower alkyl, phenyl, amino, lower alkylamino or di(lower alkyl)-amino group, with the proviso that $R_2$ is hydrogen, halogen, methyl, amino, lower alkylamino or di(lower alkyl)amino when B is a group of formula Ib, $R_3$ and $R_6$ are the same or different and each represents a hydrogen or halogen atom or a lower alkyl group, $R_4$ and $R_5$ are the same or different and each represents a hydrogen or halogen atom, an alkyl group having at most twelve carbon atoms or a lower alkoxy group, or with a mixture of the copper salt and the organic compound from which such a complex can be formed in situ.

2. A complex of copper salt, useful for treating mycoplasma induced diseases in plants and animals including humans, said copper salt having an anion substantially harmless to the subject of said treatment and said complex being with an organic compound of the formula

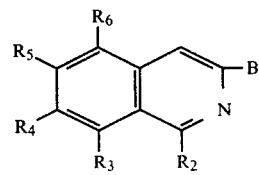

wherein B represents a group of the formula

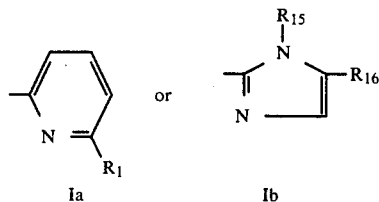

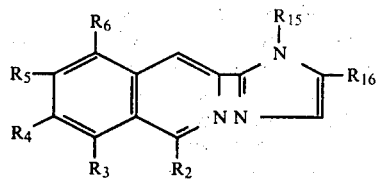

in which $R_1$ represents a hydrogen atom or a lower alkyl group, $R_{15}$ represents a hydrogen atom or a lower alkyl or lower alkenyl group and $R_{16}$ represents a hydrogen atom or a nitro group, $R_2$ represents a hydrogen or halogen atom or a lower alkyl, phenyl, amino, lower alkylamino or di(lower alkyl)-amino group, with the proviso that $R_2$ is hydrogen, halogen, methyl, amino, lower alkylamino or di(lower alkyl)amino when B is a group of formula Ib, $R_3$ and $R_6$ are the same or different and each represents a hydrogen or halogen atom or a lower alkyl group, $R_4$ and $R_5$ are the same or different and each represents a hydrogen or halogen atom, an alkyl group having at most twelve carbon atoms or a lower alkoxy group.

3. A pharmaceutical composition useful for treating mycoplasma induced diseases consisting essentially of a pharmaceutically effective amount of at least one copper complex as defined in claim 2 or of a mixture of a copper salt and an organic compound from which said complex can be formed in situ, in combination with a pharmaceutically acceptable carrier.

4. The complex of claim 2 which is bis[1-amino-3-(6-methyl-2-pyridyl)isoquinoline]cuprous nitrate.

5. A complex according to claim 2 wherein said organic compound is of the formula

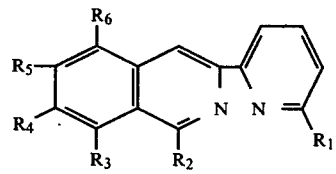

wherein each of said $R_1$, $R_2$, $R_3$, $R_4$, $R_5$ and $R_6$ groups is as defined in claim 2.

6. A complex according to claim 2 wherein said organic compound is of the formula wherein each of said $R_2$, $R_3$, $R_4$, $R_5$, $R_6$, $R_{15}$ and $R_{16}$ groups is as defined in claim 2.

7. A method according to claim 1, wherein the organic compound is a compound in which $R_2$ represents a lower alkyl or amino group, $R_6$ represents a halogen or hydrogen atom and $R_3$, $R_4$ and $R_5$ represent hydrogen atoms.

8. A method according to claim 7 or 1 wherein $R_2$ represents methyl or ethyl.

9. A method as defined in claim 1, characterized in that the copper complex or the mixture of the copper salt and the organic compound is administered to poultry in a daily dose of, or equivalent to, 25 to 100 mg of the complex per kg body weight.

10. A method as defined in claim 1, characterized in that the copper complex or the mixture of the copper salt and the organic compound is administered to pigs in a daily dose of, or equivalent to 10 to 25 mg/kg of the complex per kg body weight.

11. A method as defined in claim 1, which comprises preventing mycoplasm induced diseases of poultry by treating eggs thereof by injection with or immersion in a solution containing 1–5 g./l of said complex.

12. An animal feed composition which contains at least one copper complex as defined in claim 2 in association with an animal feed component selected from ground grains, grain by-products, animal protein, vitamins, bone meal, limestone and other inert inorganic compounds.

13. An animal feed composition according to claim 12, characterized in that it contains the copper complex in a concentration of 0.1 to 10% by weight.

14. An animal feed concentrate, which contains at least one copper complex as defined in claim 2 in association with an animal feed component selected from ground grains, grain by-products, animal protein, vitamins, bone meal, limestone and other inert inorganic compounds.

15. A feed concentrate according to claim 14, characterized in that the copper complex is present in such a concentration that the animal fodder will contain the complex in a concentration of 0.1 to 10% by weight.

16. A composition for the treatment of plants to combat mycoplasma-induced diseases thereof, containing at least one copper complex defined in claim 2 or mixture of a copper salt and an organic compound from which said complex is formed in situ in combination with an agriculturally acceptable carrier.

* * * * *